United States Patent
Spencer et al.

(10) Patent No.: US 7,090,837 B2
(45) Date of Patent: Aug. 15, 2006

(54) COMPOSITIONS AND METHODS FOR TISSUE SPECIFIC TARGETING OF LENTIVIRUS VECTORS

(75) Inventors: Brian Spencer, San Diego, CA (US); Robert Marr, San Diego, CA (US); Inder M. Verma, La Jolla, CA (US)

(73) Assignee: The Salk Institute for Biological Studies, La Jolla, CA (US)

( * ) Notice: Subject to any disclaimer, the term of this patent is extended or adjusted under 35 U.S.C. 154(b) by 94 days.

(21) Appl. No.: 10/760,123

(22) Filed: Jan. 16, 2004

(65) Prior Publication Data
US 2005/0003547 A1 Jan. 6, 2005

Related U.S. Application Data

(60) Provisional application No. 60/441,843, filed on Jan. 21, 2003.

(51) Int. Cl.
- A61K 48/00 (2006.01)
- C12N 5/00 (2006.01)
- C12N 5/15 (2006.01)
- C12N 15/63 (2006.01)
- C12P 21/06 (2006.01)

(52) U.S. Cl. .................. 424/93.2; 435/69.1; 435/320.1; 435/325; 435/455; 424/93.1

(58) Field of Classification Search .............. 435/69.1, 435/320.1, 325, 455; 424/93.1, 93.2; 514/44
See application file for complete search history.

(56) References Cited

OTHER PUBLICATIONS

Sandrin et al Blood 100(3):823-832, 2002.*
Bosch et al J. Gen. Virol. 82:2485-2494, 2001.*
Spiegel et al J. Virol. 72(6):5296-5302, 1998.*
Juengst BMJ, 326:1410-11, 2003.*
Check NATURE 422:7, 2003.*
Couzin et al, SCIENCE 307:1028, 2005.*
Rosenberg et al, SCIENCE 287:1751, 2000.*
Anderson, NATURE 392:25-30, 1998.*
Aldovini and Young, "Mutations of RNA and Protein Sequences Involved in Human Immunodeficiency Virus Type 1 Packaging Result in Production of Noninfectious Virus." *J. Virol.*, 64:1920-1926, 1990.
Chan and Kim, "HIV Entry and Its Inhibition." *Cell*, 93:681-684, 1998.
Dull et al., "A Third-Generation Lentivirus Vector with a Conditional Packaging System." *J. Virol.*, 72:8463-8471, 1998.
Feinberg et al., "The role of Tat in the human immunodeficiency virus life cycle indicates a primary effect on transcriptional elongation." *Proc. Natl. Acad. Sci. USA*, 88:4045-4049, 1991.
Finer et al., "*kat*: A High-Efficiency Retroviral Transduction System for Primary Human T Lymphocytes." *Blood*, 83:43-50, 1994.
Geigenmuller and Linial, "Specific Binding of Human Immunodeficiency virus Type 1 (HIV-1) Gag-Derived Proteins to a 5' HIV-1 Genomic RNA Sequence." *J. Virol.*, 70:667-671, 1996.
Kim et al., "A Short Sequence Upstream of the 5' Major Splice Site is Important for Encapsidation of HIV-1 Genomic RNA." *Virology*, 198:336-340, 1994.
Lamb, "Paramyxovirus Fusion: A Hypothesis for Changes." *Virology*, 197:1-11, 1993.
Leavitt et al., "Human Immunodeficiency Virus Type 1 Integrase Mutants Retain In Vitro Integrase Activity yet Fail To Integrate Viral DNA Efficiently during Infection." *J. Virol.*, 70:721-728, 1996.
Lin et al., "Receptor-Specific Targeting Mediated by the Coexpression of a Targeted Murine Leukemia Virus Envelope Protein and a Binding-Defective Influenza Hemagglutinin Protein." *Hum. Gene Ther.*, 12:323-332, 2001.
Lin and Cannon, "Use of pseudotype retroviral vectors to analyze the receptor-binding pocket of hemagglutinin from a pathogenic avian influenza A virus (H7 subtype)." *Virus Res.*, 83:43-56, 2002.
Luban and Goff, "Mutational Analysis of *cis*-Acting Packaging Signals in Human Immunodeficiency Virus Type 1 RNA." *J. Virol.*, 68:3784-3793, 1994.
McBride and Panganiban, "The Human Immunodeficiency Virus Type 1 Encapsidation Site Is a Multipartite RNA Element Composed of Functional Hairpin Structures." *J. Virol.*, 70:2963-2973, 1996.
Miyoshi et al., "Development of a Self-Inactivating Lentivirus Vector." *J. Virol.*, 72:8150-8157, 1998.
Naldini et al., "Efficient transfer, integration, and sustained long-term expression of the transgene in adult rat brains injected with a lentiviral vector." *Proc. Natl. Acad. Sci. USA*, 93:11382-11388, 1996.
Naldini et al., "In Vivo Gene Delivery and Stable Transduction of Nondividing Cells by a Lentiviral Vector." *Science*, 272:263-267, 1996.
Ory et al., "A stable human-derived packaging cell line for production of high titer retrovirus/vesicular stomatitis virus G pseudotypes." *Proc. Natl. Acad. Sci. USA*, 93:11400-11406, 1996.

(Continued)

*Primary Examiner*—Sumesh Kaushal
(74) *Attorney, Agent, or Firm*—Klarquist Sparkman, LLP

(57) ABSTRACT

This disclosure provides lentiviral vectors containing an attachment incompetent fusogenic polypeptide and a heterologous targeting polypeptide. Also provided are lentiviral packaging constructs, lentiviral packaging systems, and lentiviral gene delivery systems. Finally, methods of transducing a cell and methods of targeting a gene to a cell or tissue using the disclosed lentiviral vectors and systems are also provided.

**

OTHER PUBLICATIONS

Paillart et al., "A loop-loop "kissing" complex is the essential part of the dimer linkage of genomic HIV-1 RNA." *Proc. Natl. Acad. Sci. USA*, 93:5572-5577, 1996.

Vicenzi et al., "An Integration-Defective U5 Deletion Mutant of Human Immunodeficiency Virus Type 1 Reverts by Eliminating Additional Long Terminal Repeat Sequences." *J. Virol.*, 68:7879-7890, 1994.

Wyatt and Sodroski, "The HIV-1 Envelope Glycoproteins: Fusogens, Antigens, and Immunogens." *Science*, 280:1884-1888, 1998.

Zhang et al., "Nascent Human Immunodeficiency Virus Type 1 Reverse Transcription Occurs within an Enveloped Particle." *J. Virol.*, 69:3675-3682, 1995.

Zhang et al., "Endogenous Reverse Transcription of Human Immunodeficiency Virus Type 1 in Physiological Microenvironments: an Important Stage for Viral Infection of Nondividing Cells." *J. Virol.*, 70:2809-2824, 1996.

Zufferey et al., "Self-Inactivating Lentivirus Vector for Safe and Efficient In Vivo Gene Delivery." *J. Virol.*, 72:9873-9880, 1998.

Zufferey et al., "Multiply attenuated lentiviral vector achieves efficient gene delivery in vivo." *Nature Biotechnol.*, 15:871-875, 1997.

* cited by examiner

COMPOSITIONS AND METHODS FOR TISSUE SPECIFIC TARGETING OF LENTIVIRUS VECTORS

BACKGROUND OF THE INVENTION

This application is based on, and claims the benefit of, U.S. Provisional Application No. 60/441,843, filed Jan. 21, 2003, entitled COMPOSITIONS AND METHODS FOR TISSUE SPECIFIC TARGETING OF LENTIVIRUS VECTORS, which is incorporated herein by reference.

This invention was made with government support under grant numbers HL-53670 and AI-48034 awarded by the National Institutes of Health. The United States Government has certain rights in this invention.

This invention relates generally to methods of gene transfer and, more specifically to retroviral vectors that are specific for target cells.

Gene therapy approaches rely on efficient transfer of genes to the desired target cells. A wide variety of viral and nonviral vectors have been developed and evaluated for their efficiency of transduction, sustained expression of the transgene, and safety. Nonviral methods are inefficient and only attain a transient expression of the transgene. Viral vectors fail to achieve a satisfactory combination of efficacy of gene transfer, sustained transgene expression, and biosafety. For example, adenoviral vectors can allow highly efficient delivery of the transgene in most tissues in vivo, but expression is transient, primarily due to induction of an immune response against the transduced cells. Vectors derived from oncoretroviruses, such as the Moloney leukemia virus (MLV), exhibit characteristics favorable for sustained transgene expression and biosafety because they integrate the transgene in the genome of the target cells without transferring any viral gene. However, oncoretroviruses are severely restricted in their potential targets, as they can only transduce proliferating target cells that divide shortly after infection. Consequently, oncoretroviral vectors are limited to gene transfer in nondividing cells or employed in demanding ex vivo protocols of gene transfer. Furthermore, transcriptional shutoff of the transgene after in vivo reimplantation of the transduced cells can occur.

Lentivirus vectors based on human immunodeficiency virus (HIV) have been developed that can transduce nondividing cells both in vitro and in vivo. Such vectors can stably integrate into the host cell genome to effect long-term expression of the transgene and are free from significant cellular or humoral immune responses demonstrating their utility as delivery vehicles for genes in vivo or in vitro. As the etiological agent of acquired immunodeficiency syndrome (AIDS), safety in the use of lentiviral vectors has been enhanced through a variety of molecular engineering designs that inhibit the generation of replication-competent vectors through fortuitous recombination of vector gene components. Such engineering designs include removal of accessory genes which play a role in virulence, removal of trans-acting factors for transcription, the generation of self-inactivating vectors, separating the packaging signals from the functions required for vector production and splitting the packaging functions into multiple components. However, spectrum of infectivity of lentiviral vectors is limited to the tropism of their native envelope glycoproteins or to heterologous envelope proteins that transduce the same target cells as oncoretrovirus or other viral vectors used in gene delivery methods. Therefore, the ability to target nondividing cells, in general, and to target particular types and subclasses of nondividing cells, specifically, has been limited.

Thus, there exists a need for compositions that confer specific targeting capabilities onto lentiviral vectors and for methods of employing such vectors for the specific targeting of a therapeutic gene of interest. The present invention satisfies these needs and provides related advantages as well.

SUMMARY OF THE INVENTION

The invention provides a lentiviral vector containing an attachment incompetent fusogenic polypeptide and a heterologous targeting polypeptide. Also provided is a lentiviral packaging construct. The construct contains a nucleic acid encoding trans-acting factors sufficient for lentiviral vector generation and an attachment incompetent fusogenic polypeptide. A lentiviral packaging system having at least two nucleic acid vectors is further provided. The lentiviral packaging system consists of a first nucleic acid vector comprising a packaging construct encoding a trans-acting factor for lentiviral vector generation, and a second nucleic acid vector encoding an attachment incompetent fusogenic polypeptide, said at least two vectors together encoding trans-acting factors sufficient for lentiviral vector generation. The invention additionally provides a lentiviral gene delivery system having at least three nucleic acid vectors. The gene delivery system consists of: a first nucleic acid vector comprising a packaging construct encoding a trans-acting factor for lentiviral vector generation; a second nucleic acid vector comprising a fusogenic construct encoding an attachment incompetent fusogenic polypeptide, and a third nucleic acid vector comprising a lentiviral vector genome encoding lentiviral cis sequences sufficient for vector genome transduction, said at least three vectors together encoding trans-acting factors sufficient for lentiviral vector generation. Finally, methods of transducing a cell and methods of targeting a gene to a cell or tissue using the lentiviral vectors and systems of the invention are also provided.

DETAILED DESCRIPTION OF THE INVENTION

Figure 1:
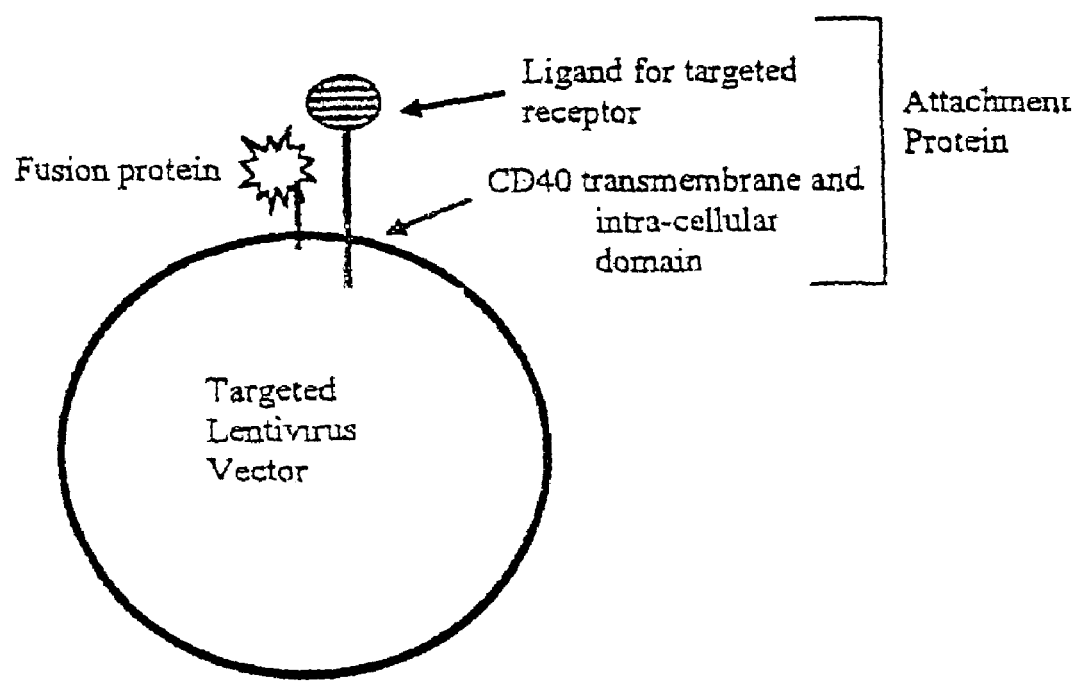
FIG. 1 shows a schematic diagram of a modular lentiviral targeting vector having a fusogenic polypeptide and a heterologous targeting polypeptide.

This invention is directed to lentiviral targeting vectors that are capable of being targeted to essentially any desired cell or tissue that contains an identifying cell surface marker. The lentiviral vectors of the invention separate the cell binding and attachment functions from the membrane fusion functions of a lentiviral envelope polypeptide. Accordingly, the lentiviral vectors of the invention are advantageous in that the infection specificity, or tropism, and the transduction activities constitute modular components of the viral vector. By separating these activities into targeting and fusogenic polypeptides, the inherent constraints associated with linked activities when modification is necessary or desired are circumvented because each activity can be separately manipulated. As such, the binding or fusion functions of the vector polypeptides can be modified, augmented, tuned or substituted as desired and according to the need of a particular purpose. The modular nature of the lentiviral vectors of the invention further allows the inclusion of one or more additional binding or fusion activities to produce multifunctional vectors having specific binding activities to different target molecules or to combine different fusion activities into the same vector. As such, the vectors offer a further advantage of multitarget capability or sequential targeting capacity.

In one embodiment, the invention is directed to a lentiviral vector containing a heterologous targeting polypeptide and a fusogenic polypeptide coexpressed on its envelope surface. The heterologous targeting polypeptide is a chimeric molecule consisting of a CD40 transmembrane domain for anchoring to the viral envelope and an affinity ligand for targeting to a cell surface receptor. One affinity ligand utilized is transferrin (Tf) which specifically targets the lentiviral vector to cells containing transferring receptor. Another affinity ligand utilized is apolipoprotein E4 (ApoE) which can specifically target the harboring vector to low density lipoprotein receptor (LDLR) expressing cells. Attachment incompetent fusogenic polypeptides include lentiviral gp41 and binding deficient, fusion competent influenza hemagglutinin (HA) polypeptide. The vectors can be produced by supplying the packaging lentiviral gene products in trans through either transient or stable transfection of cells with packaging plasmids. The vector genome can harbor a transgene for transduction into the target cell upon binding and fusion of the vector with the target cell membrane.

In another embodiment, the invention is directed to a method of gene delivery to a desired cell or tissue. The lentiviral vectors of the invention can be packaged with a vector genome containing a therapeutic or diagnostic transgene for specific in vivo delivery to target cells. Vector genomes containing the transgene and can be incorporated into the lentiviral vectors by supplying gene products for vector assembly, targeting and fusion in trans. Specific targeting is conferred by incorporation of an affinity binding molecule as the targeting polypeptide into the vector envelope that has a cognate binding molecule present on the surface of the targeted cells or tissue. Transduction and expression of the vector genome into the targeted cells is facilitated by incorporation of the fusogenic polypeptide into the vector envelope. Following administration of the lentiviral vectors, the particles will circulate and bind to cells expressing a cognate binder to its targeting polypeptide, followed by transduction and expression of the transgene. An advantage of lentiviral-based vectors is that they are capable of stably transducing non-dividing cells which allows for functional gene delivery to essentially all types of cells and tissues so long as there is an identifying targeted molecule that can be specifically or selectively bound by a targeting polypeptide. The lentiviral vectors also can be used for specific in vitro or ex vivo delivery of the transgene as well.

As used herein, the term "lentiviral vector" is intended to mean an infectious lentiviral particle. Lentivirinae or lentivirus, is a subfamily of enveloped retrovirinae or retroviruses, that are distinguishable from oncovirinae and spumavirinae based on virion structure, host range and pathological effects, for example. An infectious lentiviral particle will be capable of invading a target host cell, include an envelope and exhibit one or more characteristics of a lentivirus. Such characteristics include, for example, infecting non-dividing host cells, transducing non-dividing host cells, infecting or transducing host immune cells, containing a lentiviral virion including one or more of the gag structural polypeptides p7, p24 or p17, containing a lentiviral envelope including one or more of the env encoded glycoproteins p41, p120 or p160, containing a genome including one or more lentivirus cis-acting sequences functioning in replication, proviral integration or transcription, containing a genome encoding a lentiviral protease, reverse transcriptase or integrase, or containing a genome encoding regulatory activities such as Tat or Rev.

A lentiviral vector can exhibit some or all of the natural functions of a lentivirus. A lentiviral vector also can exhibit functions additional to, or different from, a naturally occurring lentivirus. For example, a lentiviral vector can be modified to augment or reduce a lentivirus characteristic. A lentiviral vector also can be modified to exhibit characteristics of one or more other retroviruses, retroviral vectors, host cells or heterologous cells. Modifications can include, for example, conferring additional or alternative host cell specificity such as by pseudotyping; augmenting or modulating infectivity by, for example, modifying the binding or fusion functions of an envelope polypeptide; incorporating heterologous, chimeric or multifunctional polypeptides or other membrane components into the envelope; conferring packaging or expression of non-lentivirus genomes, or conferring expression of heterologous genes onto a lentiviral vector genome. Therefore, depending of the design and incorporation of lentivirus constituent components, a lentiviral vector can be, for example, replication-competent, replication incompetent or contain some or all of the lentiviral repertoire of cis elements or trans-acting factors. As such, the term is intended to include enveloped retroviral-like particles that derive from or contain at least one functional characteristic of a lentivirus and which is capable of invading a target host cell.

As used herein, the term "lentiviral vector genome" is intended to mean a nucleic acid that encodes a lentiviral cis nucleic acid sequence required for genome packaging. A lentiviral vector genome also can encode other cis nucleic acid sequences beneficial for gene delivery, including for example, cis sequences required for reverse transcription, proviral integration or genome transcription. A lentiviral vector genome performs transduction functions of a lentiviral vector. As such, the exact makeup of a vector genome will depend on the genetic material desired to be introduced into a target cell. Therefore, a vector genome can encode, for example, additional polypeptides or functions other than that required for packaging, reverse transcription, integration, or transcription. Such functions generally include coding for cis elements required for expression of a nucleic acid of interest. The lentiviral cis sequences or elements can be derived from a lentivirus genome, a lentiviral vector genome or other virus or vector genome so long as the lentiviral vector genome can be packaged by a lentiviral vector and introduced into a target cell.

As used herein, the term "nucleic acid vector" is intended to mean any nucleic acid that functions to carry, harbor or express a nucleic acid of interest. Nucleic acid vectors can have specialized functions such as expression, packaging, pseudotyping, transduction or sequencing, for example. Nucleic acid vectors also can have, for example, manipulatory functions such as a cloning or shuttle vector. The structure of the vector can include any desired form that is feasible to make and desirable for a particular use. Such forms include, for example, circular forms such as plasmids and phagemids, as well as linear or branched forms. A nucleic acid vector can be composed of, for example, DNA or RNA, as well as contain partially or fully, nucleotide derivatives, analogs and mimetics. Such nucleic acid vectors can be obtained from natural sources, produced recombinantly or chemically synthesized.

As used herein, the term "packaging construct" is intended to mean a nucleic acid vector that encodes retroviral structural polypeptides sufficient for vector production. When used in reference to a lentiviral nucleic acid vector, the term is intended to refer to lentiviral structural polypeptides sufficient for lentiviral vector production. A lentiviral packaging construct can additionally contain other polypeptides that function in trans to facilitate, augment or supplement the efficiency of vector production or the functional characteristics of the vector particle. Structural polypeptides that function in trans for vector production included, for example, lentiviral polypeptides p6, p7, p17 and p24, which are encoded by gag and reverse transcriptase, protease and integrase, which are encoded by pol. Other trans-acting factors that can function in vector production include, for example, the polypeptides encoded by rev and tat. A packaging construct can be designed to express some or all of such trans-acting factors stably or transiently. Additionally, it should be understood that the term is intended to include construct designs that separate or split the expression of trans-acting factors, or components thereof, onto two or more nucleic acid vectors. Accordingly, a packaging construct can include multiple different nucleic acid vectors which together encode structural polypeptides sufficient for retroviral vector production.

As used herein, the term "fusogenic construct" is intended to mean a nucleic acid vector that encodes a polypeptide which facilitates or induces fusion between membranes. Therefore, the term is intended to refer to a nucleic acid vector that encodes a fusogenic polypeptide. A fusogenic construct also can encode non-fusogenic polypeptides including, for example, conferring multifunctional purposes onto the construct by encoding lentiviral transacting factors, or heterologous envelope polypeptides to alter the tropism of a lentiviral vector particle. Accordingly, a fusogenic construct also can encode packaging and pseudotype construct functions so long as it also encodes a fusogenic polypeptide. As with other constructs of the invention, a fusogenic construct also can be designed for stable or transient expression or configured so that its components are expressed from two or more nucleic acid vectors.

As used herein, the term "fusogenic polypeptide" is intended to mean a polypeptide which facilitates or induces fusion between membranes. Such polypeptides exhibit membrane fusion functions between, for example, cell-cell membranes, cell-envelope membranes, cell-vesicle membranes, envelope-vesicle membranes as well as other lipid and biochemical membranes. Specific examples of fusogenic polypeptides of the invention include, for example, lentiviral gp41, lentiviral gp160, other retroviral envelope glycoproteins or fusogenic functional fragments thereof, influenza hemagglutinin, binding defective hemagglutinin as well as other viral envelope glycoproteins or functional fragments thereof. Other fusogenic polypeptides are well known to those skilled in the art.

The term "attachment incompetent" when used in reference to a fusogenic polypeptide is intend to mean that a fusogenic polypeptide is devoid of specific targeting binding functions other than that required for membrane fusion. The fusogenic polypeptide can be devoid of non-fusion binding affinity in its natural state or can be modified to reduce or omit its non-fusion binding affinity. Specific examples of a fusogenic polypeptide devoid of non-fusion binding functions include lentivirus gp41, paramyxovirus hemagglutinin (HN) and attachment defective variants of influenza A virus hemagglutinin that are mutated at amino acid residues Y88, T126, H174, E181, L185 and G219. A triple mutant variant includes mutations at Y106, E199 and G237. Specific examples of a fusogenic polypeptides that can be altered to remove target receptor binding include lentivirus gp160, other retrovirus envelope glycoproteins and influenza virus hemagglutinin (HA). Other attachment incompetent fusogenic polypeptides, or fusogenic polypeptides that can be made to be attachment are well known to those skilled in the art.

As used herein, the term "heterologous" is intended to mean that the referenced polypeptide, nucleic acid or other molecule is derived from or associated with a species or molecule different from that being referenced. The term includes, for example, native molecules, functional fragments, as well as chimeric and multifunctional versions thereof so long as at least one portion of the referenced molecule is derived or associated with a heterologous species or a different molecule. Polypeptides, nucleic acids and other molecules that are considered heterologous to lentivirus include, for example, oncoviral and DNA virus derived molecules, mammalian derived, including human, molecules and procaryotic molecules. Specific example of heterologous polypeptides are the CD40 transmembrane domain or the affinity domain of a targeting molecule of the invention. Other polypeptides, nucleic acids or molecules that are heterologous to lentivirus are well known to those skilled in the art.

As used herein, the term "chimeric polypeptide" is intended to mean a polypeptide composed of two or more heterologous polypeptides fused together into a single primary amino acid sequence. Joinder of two or more heterologous amino acid sequences can be performed by, for example, chemical, biochemical or recombinant means. A chimeric polypeptide can therefore include, for example, a recombinant fusion protein or a chemical conjugate as well as other molecular complexes well known to those skilled in the art. When used in reference to a heterologous targeting polypeptide, the term is intended to refer to a targeting polypeptide that is composed of two or more heterologous polypeptides. For example, a chimeric targeting polypeptide can be composed of a binding domain from one molecule and a cell attachment domain from another a different molecule. Both portions of the chimeric targeting polypeptide can be derived from the same or a different species. Various other examples of chimeric targeting polypeptides are well known to those skilled in the art an are included within the meaning of the term as it is used herein.

As used herein the term "targeting polypeptide" is intended to mean a polypeptide that contains a binding partner to a molecule expressed on the surface of a targeted cell or tissue, or to a molecule that is otherwise accessible to the vector particle. Expression of a binding partner on a lentiviral vector of the invention allows the vector to be directed to, bind and attach to a predetermined target cell or tissue type. A targeting polypeptide can consist of, or include, any molecule that exhibits binding affinity forward a cognate binding partner. Therefore, targeting polypeptides can include, for example, ligands, receptors, co-receptors, counter-ligands, counter-receptors, antigens and epitopes, as well as other affinity binders well known to those skilled in the art.

As used herein, the term "ligand" is intended to mean a molecule that exhibits selective binding affinity for another molecule. Therefore, the term refers to one component of a bi- or multi-component affinity binding reaction. As one constituent of two or more interacting molecular binding species the term is intended to be neutral with reference to orientation. Therefore, a ligand can refer to all types of affinity ligands well known to those skilled in the art including, for example, ligands, haptens, counter-ligands, receptors and counter-receptors. For simplicity, and where clarity may be desired when referring to both or all components of a ligand binding reaction, reference may be made to one component as a ligand and to the cognate component counter-ligand or receptor. However, it should be understood that a ligand can be referred to equally as either a ligand or a receptor or by any other nomenclature well known to those skilled in the art which designates a pair or complex of affinity binding components. Affinity binding of a ligand can be, for example, through non-covalent or covalent interactions and can include, for example, binding affinity to polypeptides, nucleic acid, other macromolecules and small molecules. Ligands include a wide range of molecular species well known to those skilled in the art including, for example, polypeptides, nucleic acid and other macromolecules as well as small inorganic or organic molecules.

As used herein, the term "receptor" is intended to mean a molecule that exhibits selective binding affinity for another molecule. As with the term "ligand," the term "receptor" refers to one constituent of a bi- or multi-component affinity binding reaction and is intended to be neutral with reference to orientation. Therefore, a receptor can refer to all types of affinity binding molecules well known to those skilled in the art including, for example, receptors, counter-receptors, counter-ligands, ligands and haptens. Where both or all components of a receptor binding reaction are referred to herein, reference may be made to one component as a receptor and to the cognate component counter-receptor or ligand. However, it is understood that a receptor can be referred to equally as either a receptor or a ligand or by any other nomenclature well known to those skilled in the art which designates a pair or complex of affinity binding components. Binding of a receptor to its partner can be, for example, through non-covalent or covalent interactions and can include, for example, binding affinity to polypeptides, nucleic acid, other macromolecules and small molecules. Receptors include a wide range of molecular species well known to those skilled in the art including, for example, polypeptides, nucleic acid and other macromolecules as well as small inorganic or organic molecules.

Lentiviruses are a family of retroviruses that are characterized by the slow progression of disease. This family includes, for example, human HIV-1 and HIV-2, simian immunodeficiency virus (SIV), bovine immunodeficiency virus (BIV), feline immunodeficiency virus (FIV), caprine arthritis encephalitis virus (CAEV) and equine infectious anemia virus (EIAV). Disease presentation can occur in many forms including, for example, tumors, infections due to viral induced immunodeficiency as well as encephalitis, wasting, pneumonia and arthritis. Lentiviral infections are persistent because of the ability to integrate their genome into the host chromosome and their ability to evade host immune responses.

The lentivirus is an icosahedral enveloped virus having a diploid RNA genome that becomes integrated into the host chromosome as a proviral DNA for genome replication. The lentiviral genome contains gag, pol and env genes which encode the structural polypeptides of the virion (p17, p24, p7 and p6); the viral enzymes protease, reverse transcriptase and integrase, and the envelope glycoproteins (gp120and gp41), respectively. The lentiviral genome also encodes two regulatory polypeptides (Tat and Rev) and four accessory polypeptides that play a role in virulence (Vif, Vpu, Vpr and Nef). Unlike other retroviruses, lentiviruses have the ability to efficiently infect and transduce non-proliferating cells, including for example, terminally differentiated cells. Lentiviruses also have the ability to efficiently infect and transduce proliferating cells. Despite the pathogenesis associated with lentiviruses, it is well known to those skilled in the art that the undesirable properties of lentiviruses can be recombinantly separated so that its beneficial characteristics can be harnessed as a delivery vehicle for therapeutic or diagnostic genes. Therefore, lentiviral-based vectors can be produced that are safe, replication-defective and self-inactivating while still maintaining the beneficial ability to transduce non-dividing cells and integrate into the host chromosome for stable expression. A description of the various different modalities of lentiviral vector and packaging systems for vector assembly and gene delivery can be found in, for example, in Naldini et al., *Science* 272:263–267 (1996); Naldini et al., *Proc. Natl. Acad. Sci. USA* 93:11382–11388 (1996); Zufferey et al., *Nature Bio.* 15:871–875 (1997); Dull et al., *J. Virol.* 72:463–8471 (1998); Miyoshi et al., *J. Virol.* 72:8150–8157 (1998), and Zufferey et al., *J. Virol.* 72:9873–9880 (1998).

The invention provides a lentiviral vector consisting of an attachment incompetent fusogenic polypeptide and an heterologous targeting polypeptide.

The lentiviral vectors of the invention are viral particles that have the ability to bind to and introduce genetic material into a target cell. The vectors have adopted the beneficial characteristics of lentivirus and can be used as a delivery vehicle for any genetic material that is within a packagable size for a lentivirus. Particle binding and introduction of genetic material by a lentiviral vector is similar to infection and transduction of a susceptible cell by a virus. However, because the vectors can be made replication incompetent, they can be rendered incapable of lateral infection into adjacent cells. Hence, transduction of a target cell with a replication incompetent vector is vertical in nature where the vector's genome is expressed only in those cells actually transduced.

The tropism of retroviruses is dictated by the viral envelope polypeptide. Cell type specificity for infection and propagation of viruses therefore depends on the cell-associated binding partner to the envelope polypeptide. Once an envelope polypeptide comes in contact with its receptor, virus attachment and infection proceeds. The lentiviral vector particles of the invention utilize such a binding and attachment process to target, infect and transduce desirable cell types and tissues. In this regard, the lentiviral vectors of the invention are engineered to express on their vector envelope a heterologous targeting polypeptide that is a binding partner to a molecule expressed on the surface of a targeted cell or tissue, or to a molecule that is otherwise accessible to the vector particle. By expression of a binding partner, the lentiviral vectors can bind and attach to a predetermined target cell or tissue type. Specificity of targeting for the vectors of the invention therefore results from designing a vector to contain a predetermined binding molecule that has an affinity binding counterpart on the desired targeted cell or tissue.

Being able to specify the targeting capabilities of the lentiviral vectors of the invention results in a modular delivery vehicle for genes or other compounds. The vector architecture remains as a foundational structure to which different targeting molecules can be incorporated to confer a desired binding specificity. In similar fashion, the framework of the vector genome, or its functional elements, can remain constant but amenable to substitution by different transgenes for their expression in a target cell.

The lentiviral vector architecture can be devoid of the lentivirus Env polypeptide and any of a variety of affinity binding polypeptides can be incorporated into the envelope structure to confer a predetermined targeting specificity. The vectors can be generated to harbor a single targeting polypeptide species to confer a single, unique binding specificity or multiple targeting polypeptide species can be incorporated to confer two or more different binding specificities. Therefore, the vectors can be designed or engineered to combine a predetermined binding specificity with the vector particle to change, modulate or augment its targeting capabilities to achieve a desired outcome.

Desirable targeting specificities can include highly specific lentiviral targeting vectors as well as broad spectrum targeting vectors. For example, highly specific, or monospecific, lentiviral targeting vectors of the invention can be generated, for example, by using a heterologous targeting polypeptide that has a corresponding binding partner specific to a particular cell type or tissue. In contrast, broad spectrum targeting vectors can be generated by using a heterologous targeting polypeptide that has a cognate binding partner on multiple different cell types or tissues or by using multiple different heterologous targeting polypeptides that have specificities to different cell types or tissues. Being able to engineer a single specificity to a unique target cell marker, multiple specificities unique to different target cells or a single specificity to a ubiquitous marker provides the lentiviral vectors of the invention with flexible and versital targeting capabilities because they can be tailored for many different targeting and delivery applications.

Highly specific lentiviral targeting vectors can be useful as delivery vehicles for therapeutic or diagnostic nucleic acids or other compounds when, for example, it is desirable to target a particular tissue, a particular class of cell types, a particular cell type or one or more particular subtypes of any of these categories. Such specific lentiviral vectors can be generated with a heterologous targeting polypeptide that exhibit binding affinity to a unique cognate binding partner on the targeted tissue, class, cell type or subtype for the delivery of a therapeutic or diagnostic molecule. Broad spectrum or ubiquitous targeting vectors can be useful as delivery vehicles for therapeutic molecules when, for example, pathogenesis or the causative agent is pleiotropic in nature. Ubiquitous targeting vectors also are useful as delivery vehicles for diagnostic molecules to, for example, identify regions of pathogenesis or to ascertain the cause or symptoms of an aberrant condition. As described further below, the therapeutic or diagnostic nucleic acids or compounds include, for example, an encoding nucleic acid such as a transgene, that when expressed in the targeted cell or tissue produces a polypeptide having the desired therapeutic or diagnostic activity.

Desirable targeting specificities also can include bi-specific and multi-specific lentiviral targeting vectors. Lentiviral vectors can be generated that incorporate two or more heterologous targeting polypeptides to achieve bi- and multi-specific targeting capabilities. Each heterologous targeting polypeptide can exhibit binding specificity to a cognate binding partner on the targeted cell or cells. Alternatively, such multi-specific vectors also can be generated by employing a single heterologous targeting polypeptide which exhibits bi-functional or multi-functional binding capabilities. For example, a heterologous targeting polypeptide that binds to two different ligands through the same binding domain and a heterologous targeting polypeptide that contains two different binding domains to different ligands will confer bi-specific targeting capabilities onto the lentiviral vector. Additionally, hierarchical combinations also can be generated by combining various bi- and multi-functional heterologous targeting polypeptides to achieve essentially any combination of desired binding specificity. The configuration of heterologous targeting polypeptides within a lentiviral vector of the invention can therefore include from one to many different species to achieve a desirable targeting specificity for a particular application. As described further below, the flexible targeting capabilities of the vector provides the user with the capacity to deliver genes or other compounds simultaneously or sequentially to the same or different targets.

The specificity of the lentiviral vectors of the invention will depend, in part, on the binding specificity of the heterologous targeting polypeptide and on the uniqueness of the cognate binding partner of the target cell or tissue. For example, the greater the specificity of the heterologous targeting polypeptide for the target binding partner, the less cross-reactivity with non-target molecules and cells. Binding specificity is determined by a number of factors well known to those skilled in the art and includes, for example, binding affinity and avidity of the heterologous targeting polypeptide to the targeted binding partner. For example, a low affinity targeting polypeptide can have high specificity because it is multivalent. Similarly, the specificity of a heterologous targeting polypeptide exhibiting high affinity toward its cognate binding partner can be further increased by increasing its copy number or valency.

As described above, in order to specifically target the lentiviral vectors of the invention to a desired cell type or tissue, the affinity of a heterologous targeting polypeptide of the vector can vary according to the particular application. For abundant targets, for example, the affinity of the targeting polypeptide can be lower compared to a targeting polypeptide against a less abundant target and still achieve the same level of specificity. Targeting polypeptide binding affinities sufficient to achieve specific lentiviral vector targeting can range between, for example, about $10^6$ $M^{-1}s^{-1}$ to about $10^{11}$ $M^{-1}s^{-1}$. Binding affinities of a targeting polypeptide also can be, for example, above or below this range while still achieving sufficient binding specificity. For example, the higher the affinity constant, the greater specificity of binding that can be achieved. Accordingly, targeting polypeptide binding affinities sufficient for specific targeting can be, for example, $10^{-7}$, $10^{-8}$, $10^9$ or $10^{10}$ $M^{-1}s^{-1}$, as well as any affinity constant between these numbers. Specific examples include the heterologous targeting polypeptides transferrin and apolipoprotein E4 which have good affinity constants for their binding partners. Those skilled in the art will know, or can readily determine what targeting polypeptide affinity is sufficient to achieve specific binding of a lentiviral vector given the teachings and guidance provided herein.

The uniqueness of the cognate binding partner also influences the specificity of a heterologous targeting polypeptide for its targeted cell or tissue. For example, a cognate binding partner found only on the target cell or tissue will uniquely identify the targeted cell or tissue. Similarly, a cognate binding partner selectively found on the target cell or tissue will preferentially identify the target cell or tissue over other cells and tissues. Conversely, a cognate binding partner that is prevalent on a variety of cells or tissues will result in targeting of the lentiviral vector to all cells expressing the common marker. Given the teachings and guidance provided herein, those skilled in the art will know, or can determine, which targeted markers are unique, selective or prevalent and which of such targets can be useful for a particular application.

It should be understood that the targeting capabilities of the lentiviral vectors of the invention are not limited to prior knowledge or empirical determination of a unique marker for specific and unique targeting of a particular cell type or tissue. As described previously in reference to tailoring the specificity of a lentiviral vector, the principle of combining or mixing and matching heterologous targeting polypeptides toward different target cell markers can be used both to expand as well as to narrow the scope of targeting capabilities. For example, multiple binding specificities can be used to narrow the targeted cell type by binding to a combination of target markers that together uniquely or selectively identify the target cells or tissue. Therefore, the availability of a unique marker is not a prerequisite for unique targeting.

Nor is the availability of a heterologous targeting polypeptide that is specific for a cognate binding partner a prerequisite for unique and specific targeting of the lentiviral vectors of the invention. Instead, a set or combination of heterologous targeting polypeptides can be generated that have sufficient binding specificity toward a panel of target cell markers such that the binding combination can distinguish the targeted cells from unwanted or undesirable cells or tissues. Those skilled in the art will know, or can readily determine a particular combination of targeting polypeptide binding specificity and combination of targeted binding partners that will achieve unique, selective or ubiquitous lentiviral vector specificity.

Engineering a predetermined binding specificity into the vector can be achieved by incorporating into a vector envelope a targeting polypeptide having a desired binding specificity. Because lentivirus are enveloped viruses, a targeting polypeptide can be incorporated by, for example, normal cellular processes for transmembrane insertion, or for membrane attachment or anchoring, of polypeptides, lipids and other macromolecules. For example, a targeting polypeptide can contain a transmembrane domain or a membrane attachment domain that incorporates into, or is capable of incorporating into, a lentiviral vector envelope. Alternatively, a targeting polypeptide can contain a membrane anchoring domain that signals attachment to, for example, a lipid anchor. Nucleic acids encoding a particular targeting polypeptide can be generated by recombinant methods or chemical synthesis and then expressed in a vector packaging system for automatic incorporation into a lentiviral vector envelope. Alternatively, a particular targeting polypeptide can be produced in vitro or chemically synthesized and then incorporated into a vector envelope using a cell-free system. Therefore, the targeting polypeptides of the invention include integral membrane polypeptides, peripheral membrane polypeptides as well as those polypeptides anchored by other non-polypeptide molecules or macromolecules.

Other methods known to those skilled in the art also can be used for incorporation or attachment of a targeting polypeptide into a lentiviral vector of the invention. Such other methods include, for example, the non-covalent association of a targeting polypeptide with a envelope associated polypeptide, lipid, carbohydrate or other molecule, or chemical conjugation. Therefore, incorporation can be accomplished using a variety of methods well known to those skilled in the art.

A targeting polypeptide can be, in whole or in part, heterologous or homologous to a lentiviral polypeptide so long as it can incorporate, or be made to incorporate, into a vector envelope of the invention. For example, a heterologous targeting polypeptide can be derived from a species other than lentivirus or derived from a molecule different from the lentivirus gp160 or gp120 envelope polypeptides. Where a targeting polypeptide is heterologous, it is sufficient for at least one portion of the targeting polypeptide to be derived from a non-lentiviral species or non-lentiviral envelope polypeptide.

As described further below, targeting polypeptides useful in the lentiviral vectors of the invention include those polypeptides that exhibit binding affinity toward a cognate binding partner on a target of interest. A targeting polypeptide can include, for example, an affinity ligand, a receptor, an antibody, counter-ligand or counter-receptor so long as it exhibits binding affinity toward a cognate binding partner. Specific examples of targeting polypeptides include, for example, transferrin, an apolipoprotein, Rabies G glycoprotein and lentivirus gp120.

Various other binding polypeptides well known to those skilled in the art can be used as a targeting polypeptide in the lentiviral vectors of the invention. Given the teachings and guidance provided herein, those skilled in the art can obtain or synthesize an encoding nucleic acid for a binding polypeptide, adapt it for incorporation into a lentiviral vector envelope and express it in a packaging system to generate a lentiviral vector having that binding polypeptide as a targeting polypeptide.

A targeting polypeptide also can include functional fragments and domains thereof that retain target binding affinity or specificity. Such functional fragments or domains can be, for example, a ligand or receptor binding portion of the native targeting polypeptide which excludes, for example, other binding domains, other functional domains such as signal transduction domains, or single chain derivatives of heteromeric binding polypeptides. Functional fragments or domains of targeting polypeptides can be combined with other functional fragments from, for example, heterologous polypeptides to confer additional activities onto the targeting polypeptide. The additional activities can include other target binding activities or membrane attachment activity, for example.

The invention further provides for chimeric targeting polypeptides. A chimeric targeting polypeptide can be a heterologous targeting polypeptide that contains a membrane attachment domain and a targeting domain.

A chimeric targeting polypeptide can be incorporated into a lentiviral vector of the invention where one portion confers target binding specificity and another portion confers envelope incorporation or attachment function. Various membrane attachment domains can be joined with a targeting polypeptide, or a functional fragment thereof, to produce a chimeric targeting polypeptide for the vectors of the invention. Such membrane attachment domains can include, for example, lentiviral gp41, the transmembrane domain of CD40, VSV-G, gp120 or CD4. The chimeric targeting polypeptide can be generated by joining nucleic acids encoding the membrane attachment and target binding domain portions and expressing the encoding chimeric nucleic acid in a vector packaging system.

The modular targeting capabilities of the lentiviral vectors of the invention described previously can be achieved by separating the binding functions of the envelope polypeptide from its fusion functions. An env gene of a lentivirus encodes a 160 Kd polypeptide that confers both of these activities (gp160). The gp160 polypeptide is a bifunctional molecule expressed on the viral envelope and contains a gp120 polypeptide constituent that exhibits attachment activity and a gp41 polypeptide that exhibits envelope fusion activity. Upon binding of gp 160 to its natural target, through its gp120 component, a conformational change is induced in the molecule which signals activation of the gp41 component and subsequent envelope fusion. For a description of lentiviral binding and cell fusion see, for example, Chan and Kim, *Cell* 93:681–684 (1998), and Wyatt and Sodroski, *Science* 280:1884–88 (1998).

The lentiviral vectors of the invention have circumvented this multi-step process employing a bifunctional molecule by separating the fusion and binding functions into different molecules separately incorporated into the vector envelope. As such, the vectors of the invention can be generated which combine essentially any fusogenic molecule with essentially any affinity binding molecule to match a desired targeting specificity with a desired fusion capability.

Fusogenic molecules that can be incorporated into the lentiviral vectors of the invention can include, for example, lentiviral gp41or a binding defective influenza hemagglutinin. As described above, gp41 contains the membrane or envelope attachment domain of gp160. This portion of the envelope polypeptide also contains a domain that facilitates vector envelope fusion with target cell membrane.

Binding defective influenza hemagglutinin consists of a number of variants of influenza hemagglutinin that exhibit reduced binding affinity for its ligand but maintain membrane fusion functions. Specific examples include variants of influenza A virus hemagglutinin that are mutated at amino acid residues Y88, T126, H174, E181, L185 and G219, as described, for example, in Lin et al., *Human Gene Ther.* 12:323–332 (2001), and Lin and Cannon, *Virus Res.*, 83:43–56 (2002). Within this family of binding defective influenza hemagglutinins is a variant that exhibits essentially no attachment activity but contains complete fusogenic functions. This variant contains triple substitutions at Y88F, E181Q and G219K.

Paramyxovirus hemagglutinin (HN) is another fusogenic polypeptide that can be incorporated into the lentiviral vectors of the invention. For example, HN exhibits fusion activity while being devoid of receptor binding activity (Lamb, R. A., *Virology* 197:1–11 (1993). Other fusogenic polypeptides well known to those skilled in the art can similarly be used in the vectors of the invention. Any of these fusogenic polypeptides, or functional fragments thereof that retain fusogenic function can be utilized in the lentiviral vectors of the invention to promote vector fusion and transduction of target cells or tissues. Various other fusogenic polypeptides are well known to those skilled in the art and can similarly be incorporated into the vectors, or used in the systems, of the invention.

As with incorporation of the heterologous targeting polypeptides of the invention, incorporation of fusogenic polypeptides can be achieved by, for example, normal cellular processes for transmembrane insertion, or for membrane attachment or anchoring, of polypeptides, lipids and other macromolecules. Many fusogenic polypeptides are membrane associated. As such, they can contain a transmembrane domain or a membrane attachment domain that naturally functions to incorporate it into a membrane or vector envelope. Alternatively, a fusogenic polypeptide can be modified to contain a membrane anchoring domain such as a transmembrane domain or a lipid attachment signal. Nucleic acids encoding a particular fusogenic polypeptide can be generated by, for example, recombinant methods or chemical synthesis and then expressed in a vector packaging system for automatic incorporation into a lentiviral vector envelope. Similarly, modifications or engineered designs of particular fusogenic polypeptides also can be accomplished, for example, in the encoding nucleic acid and then expressed for incorporation into a lentiviral vector envelope. Therefore, the fusogenic polypeptides of the invention include integral membrane polypeptides, peripheral membrane polypeptides as well as those polypeptides anchored by other non-polypeptide molecules or macromolecules. Given the teachings and guidance provided herein, those skilled in the art will know how to express or adapt a particular fusogenic polypeptide for incorporation in the compositions or methods of the invention.

The invention also provides a lentiviral packaging construct. The packaging construct contains a nucleic acid encoding trans-acting factors sufficient for lentiviral vector generation and an attachment incompetent fusogenic polypeptide.

The design of a viral vector system for therapeutic or diagnostic gene delivery can be based on the segregation of the viral genome of cis-acting sequences involved in its transfer to target cells from trans-acting sequences encoding the viral polypeptides. The vector particle is assembled by viral polypeptides expressed from nucleic acid constructs stripped of cis-acting sequences. The cis sequences are instead incorporated into a nucleic acid vector for expression of the transgene to create the vector's genome. This vector genome, or transducing vector, is endowed with a full complement of cis-acting sequences which allows its encapidation and transfer to the target cell. Because the particle will transfer only the vector genome, the target cell will be devoid of trans-acting polypeptides needed for further vector particle production and the infection process is limited to a single round without spreading. By separating the cis- and trans-acting viral functions, a safe and efficient lentiviral vector system can be produced. For the particular use of lentiviral-based vectors in therapeutic or diagnostic applications, it can be desirable to separate many, if not all of the cis- and trans-acting functions, of the vector genome from the packaging system nucleic acid constructs.

Several cis sequences have been implicated in the encapsidation and dimerization of lentiviral viral RNA. For example, the packaging signal or Ψ sequence, located in the untranslated leader downstream of the major splice donor site, contributes to RNA packaging and discrimination of genomic from spliced transcripts. Additional sequences contributing to encapsidation and genome discrimination have been identified in the transcribed long terminal repeats (LTR) and 59 nucleotide (nt) leader sequence upstream of the major splice donor site. Lentiviral packaging signal sequences can be found described in, for example, Lever et al., *J. Virol.* 70:721–28 (1989); Aldovini and Young, *J. Virol.* 63:1920–26 (1990); Luban et al., *J. Virol.* 68:3784–93 (1994); Kim et al., *Virology* 198:336–40 (1994); Vicenzi et al, *J. Virol.* 68:7879–90 (1994); Geigenmuller et al., *J. Virol.* 70:667–71 (1996); Paillart et al., *Proc. Natl. Acad Sci. USA*, 93:5572–77 (1996), and McBride and Panganiban, *J. Virol.* 70:2963–73 (1996). Therefore, depending on the desired efficiency, a lentiviral packaging signal included in a vector genome of the invention can be, for example, a lentiviral Ψ sequence alone or a multipartite signal consisting of a Ψ sequence together with packaging determinants within its transcribed LTR leader sequence.

Features of the lentiviral packaging constructs that prevent their transfer to target cells include a several modifications to the viral sequence. Modifications at the 5' end of the viral genome delete or disrupt structural motifs implicated in RNA encapsidation and dimerization. For example, deletion of the 5' leader sequence reduces the encapsidation efficiency of lentiviral transcripts whereas removal of both LTRs and of the primer binding site from the packaging construct prevents reverse transcription and integration of any encapsidated transcript. The complement of gene product functions that can be included in a packaging construct or system can range from those lentiviral gene products necessary to achieve encapsidation to the full repertoire of trans-acting functions encoded in a lentiviral genome.

One mode of the packaging constructs and systems of the invention precludes the generation of replication-competent HIV viruses, even by unlikely rearrangement and recombination events because of the actual absence of most of HIV env sequences in any of the packaging constructs or vector genomes. The use of a separate construct encoding a heterologous targeting polypeptide, or an additional envelope polypeptide, makes it unlikely that a replication-competent recombinant be generated. This unlikely event would require multiple recombination events between different construct plasmids and/or endogenous retroviral sequences, including recombination between nonhomologous sequences.

As described further below, the lentiviral packaging constructs, systems and gene delivery systems incorporate the above-described considerations and functional requirements for component nucleic acid vectors needed to generate a vector of the invention. For production of a lentiviaral vector of the invention, a lentiviral packaging construct can be generated which encodes trans-acting factors sufficient for lentiviral vector generation as described above and an attachment incompetent fusogenic polypeptide. Trans-acting factors sufficient for vector generation include, for example, the polypeptides encoded by the lentiviral gag, pol and rev genes. One or more of the lentiviral trans-acting factors can be encoded on a separate nucleic acid construct, such as a plasmid, such that the packaging construct consists of two or more plasmids. The separation of trans-acting factors onto separate plasmids further ensures against unwanted recombination events.

The attachment incompetent fusogenic polypeptide can be, for example, any of those polypeptides described previously. Briefly, the packaging constructs can encode in an expressible fashion gp41, a binding defective influenza hemagglutinin polypeptide, paramyxovirus HN, functional fragments thereof, or other fusogenic polypeptides known to those skilled in the art. Such fusogenic polypeptides will be incorporated into a nascent vector particle upon expression in a packaging cell together with trans-acting factors required for vector generation. Given the teachings and guidance provided herein, the packaging construct can be generated from the encoding nucleic acids using methods well known to those skilled in the art.

Similarly, a lentiviral packaging construct of the invention also can contain a nucleic acid encoding a heterologous targeting polypeptide. As described previously, the encoding targeting polypeptide nucleic acid can be additional to, or replace the envelope polypeptide native to lentivirus. Additionally, it can augment, substitute or replace any envelope polypeptide used pseudotype a lentiviral vector. Therefore, the packaging construct can encode, for example, one or more heterologous targeting polypeptides to impart onto the resultant vector essentially any predetermined targeting specificity. As with fusogenic polypeptides, the packaging construct also can encode a heterologous targeting polypeptide that is operatively linked to a promoter or other expression elements that direct its expression in a packaging cell or system. Heterologous targeting polypeptides, including chimeric heterologous targeting polypeptide include, for example, those described previously as well as other binding polypeptides known to those skilled in the art. Such heterologous targeting polypeptides will be subsequently incorporated into a vector particle upon expression with trans-acting factors required for vector generation.

Various combinations and permutations of nucleic acid vectors encoding a functional complement of lentiviral trans-acting factors, fusogenic polypeptide and heterologous targeting polypeptide can be generated to produce a vector packaging system. Briefly, encoding nucleic acids for components needed to produce functional lentiviral vector can be divided into two or more nucleic acid vectors. The nucleic acid vectors can, for example, encode different trans-acting factors such that together they constitute a packaging construct as described previously. One of the component nucleic acid packaging vectors can encode a desired fusogenic polypeptide and a heterologous targeting polypeptide. Alternatively, each of the component nucleic acid packaging vectors can separately encode a fusogenic polypeptide and a heterologous targeting polypeptide.

Another combination for a packaging system can include, for example, a packaging construct that encodes lentiviral trans-acting factors and a second nucleic acid vector that encodes either or both a fusogenic polypeptide and a heterologous targeting polypeptide. The packaging construct can be further divided, for example, into two or more nucleic acid vectors which further separate the trans-acting factors on different nucleic acids. In one specific embodiment, a packaging system of the invention consists of one component nucleic acid packaging vector encoding lentiviral gag and pol genes, a second component nucleic acid packaging vector encoding a lentiviral rev gene and a third nucleic acid vector encoding a heterologous targeting polypeptide having a predetermined binding specificity. A nucleic acid encoding a fusogenic polypeptide can be included on any one of the above described vectors. Various other combinations of encoding nucleic acids and nucleic acid vectors that includes the combination of trans-acting lentiviral polypeptides sufficient for vector assembly, a fusogenic polypeptide and a heterologous targeting polypeptide can be constructed by one skilled in the art to produce a lentiviral packaging system of the invention. Expression of the packaging system constructs and nucleic acid vectors in a cell results in co-expression of the complement of encoded nucleic acids self-assembly of lentiviral vectors therefrom.

The lentiviral packaging constructs or lentiviral packaging systems of the invention can additionally include a vector genome to produce a lentiviral gene delivery system. Whether a packaging vector or system consists of a single, double, triple or higher order nucleic acid vector format, inclusion of a nucleic acid vector encoding cis sequences sufficient for packaging and expression of a transgene completes a system of nucleic acid vectors can produce a lentiviral vector harboring a vector genome of interest. Therefore, depending on the format chosen for the packaging construct or system, a lentiviral gene delivery system of the invention can consist of two, three, or four or more nucleic acid vectors.

As described previously, the packaging constructs and systems express those components sufficient for vector particle generation. Inclusion of a vector genome containing an expressible transgene in the vector production system will result in its encapsulation into the resultant vector particles. Specific cis sequences sufficient for encapsulation include, for example, the psi signal and related packaging sequences and some or all of the 5' and 3' LTRs for reverse transcription into a proviral DNA and integration into a host chromosome.

The expression control elements of a vector genome can vary depending on the cell or tissue type to be targeted or depending on the desired level of control over the nucleic acid once transduction of a host cell has been accomplished. For example, it is beneficial to utilize promoter and gene regulatory elements that are operative in the target cell type. Moreover, greater levels of specificity can be effected where a target cell compatible tissue specific promoter or regulatory element is used to drive expression of the transgene. Further, the expression can be either inducible or constitutive. Moreover, the vectors can be self-inactivating to prevent proviral RNA expression once chromosome integration has occurred. All of such considerations are well known to those skilled in the art of recombinant gene expression and gene delivery. Therefore, those skilled in the art will know what combinations or modifications of the considerations are desirable given a particular gene delivery application for a lentiviral vector of the invention.

Thus, the invention further provides a lentiviral packaging system that has at least two nucleic acid vectors. The packaging system consists of a first nucleic acid vector consisting of a packaging construct encoding a trans-acting factor for lentiviral vector generation, and a second nucleic acid vector encoding an attachment incompetent fusogenic polypeptide, where the at least two vectors together encoding trans acting factors sufficient for lentiviral vector generation. A lentiviral gene delivery system having at least three nucleic acid vectors is also provided. The gene delivery system consists of (a) a first nucleic acid vector consisting of a packaging construct encoding a trans-acting factor for lentiviral vector generation; (b) a second nucleic acid vector consisting of a fusogenic construct encoding an attachment incompetent fusogenic polypeptide, and (c) a third nucleic acid vector comprising a lentiviral vector genome encoding lentiviral cis sequences sufficient for vector genome transduction, where the at least three vectors together encoding trans-acting factors sufficient for lentiviral vector generation.

The invention additionally provides a method of transducing a cell. The method consists of contacting a cell expressing a target receptor with an effective amount of a lentiviral vector having a cell surface attachment incompetent fusogenic polypeptide and a heterologous targeting polypeptide under conditions sufficient for said lentiviral vector to fuse with said cell.

Infection of a target cell with a lentiviral vector is similar to a retroviral infection process. Once the content of a lentiviral vector is delivered inside the target cell, uncoating, reverse transcription, interaction with cytoplasmic chaperones and the nuclear import machinery, and maturation to an integration-competent complex takes place. The lentiviral vectors of the invention can therefore be used to transduce a cell with a transgene of interest. The lentiviral vectors of the invention also can be used to specifically target and deliver a transgene to a predetermined cell or tissue type. A lentiviral vector of the invention can function for either transduction or targeted transduction of a specific cell or tissue type. To effect transduction or targeting, the vector can contain a targeting polypeptide having a cognate binding partner on the cells to be transduced or targeted and a fusogenic polypeptide. The targeting polypeptide can be, for example, heterologous, chimeric or both. The various combinations and permutations of targeting polypeptides and fusogenic polypeptides described previously are applicable to methods of using lentiviral vectors for specific, preferential or ubiquitous delivery of a therapeutic gene of interest.

For transduction of a cell or cell population is contacted with an effective amount of a lentiviral vector having incorporated into its envelope a fusogenic polypeptide and a heterologous targeting polypeptide which can bind to the cell or population. An effective amount is that amount sufficient for sufficient for vector binding and cell fusion. An effective amount of vector is between about 1 ng-100 µg, generally, an effective amount is about 100 ng-50 µg, and more generally an effective amount is about 1–10 µg. Conditions that are sufficient for transduction include essentially any physiologically compatible medium. Such conditions include, for example, cell culture medium and sterile physiological medium. Incubation times sufficient for transduction can range from about minutes, generally about 1–4 hrs, and more generally about 5–24 hrs. Other vector amounts and conditions sufficient for vector-cell fusion are well known to those skilled in the art and can similarly be used in the methods of the invention for transducing a cell or cell population using the lentiviral vectors of the invention.

Targeting a gene to a cell or tissue also can be accomplished by administering a lentiviral vector expressing on its surface an attachment incompetent fusogenic polypeptide and a heterologous targeting polypeptide having binding affinity for a cognate target cell binding molecule. As described previously, the cognate target cell binding molecule can be, for example, a receptor, a ligand, a counter-receptor, a counter-ligand or other macromolecule or molecule to which a targeting polypeptide can specifically or selectively bind.

An effective amount of the lentiviral vectors can be administered to a subject having a cell or tissue containing the cognate binding partner. An effective amount includes, for example, less than one infectious unit, to between one and several infectious units, to many infectious units. Administration can be accomplished by, for example, intravenous, intraperitoneal, subcutaneous or other methods well know to those skilled in the art. Because the lentiviral vectors of the invention are based on affinity for a targeted marker, they will circulate in the subject until coming in contact and binding with the cognate targeted marker. Following binding, the vector envelope will fuse with the target cell via its fusogenic polypeptide and deliver its contents.

Additionally, the vector particles can be subjected to various pre-treatments to enhance infectivity. For example, vector genome DNA synthesis can be promoted inside the intact lentiviral vector by exposure to dNTPs and magnesium chloride. Moreover, the the efficiency of the reaction can be increased by the addition of the polyamine spermine and spermidine. See, for example, Zang et al., *J. Virol.* 69:3675–82 (1995) and Zang et al., *J. Virol.* 70:2809–2824 (1996). Lentiviral vectors pre-treated in such a way exhibit increased infectivity of target cells, especially where reverse transcription activity can be a rate-limiting step. Pre-stimulation of reverse transcription also can be used to increase the transduction efficiency of lentiviral vectors in both dividing and non-dividing target cells. Depending on a particular application, such treatments can be performed before during or after use of a lentiviral vector of the invention. Additionally, such treatments can be performed successively, in parallel or simultaneous with the same or a different treatment which augments the efficiency of infection or transduction. Those skilled in the art know, or can determine, other treatments that augment the efficiency of vector infection, transduction or both given the teachings and guidance provided herein.

Specific examples of targeting vectors include a lentiviral vector that can cross the blood brain barrier via the transferrin or LDL receptor. Lentiviral vectors containing either the transferrin or ApoE targeting polypeptides and either the HAtmt or gp41 fusion protein can be delivered systemically to a subject via injection. The vectors will bind and cross the blood brain barrier via targeting of the transferrin receptor therein. Once across the barrier, the vectors can additionally contain a second heterologous targeting polypeptide that is specific to the neuronal cell type of interest. In such a fashion, specific therapeutic or diagnostic genes can be delivered in a two-step targeting procedure that will enable the specific delivery of desirable genes to non-dividing neuronal cells and tissue.

The lentiviral vectors and methods of the invention additionally are applicable to numerous other therapeutic and diagnostic procedures. For example, the ability to target the lentiviral vectors for gene therapy to specific organs other than the brain, will be useful for such diverse diseases as diabetes (pancreas), cystic fibrosis (lung), or hemophilia (liver or hematopoietic stem cells). In addition, the ability to specifically modify the tropism of the lentivirus is beneficial, for example, in the delivery of genes to other animals that are currently studied as models. Such models include, for example, zebrafish and drosophila.

Therefore, the invention also provides a method of targeting a gene to a cell or tissue. The method consists of administering to a subject having a cell or tissue expressing a target receptor with an effective amount of a lentiviral vector having a cell surface attachment incompetent fusogenic polypeptide and a heterologous targeting polypeptide under conditions sufficient for said lentivirus to bind to said target receptor.

It is understood that modifications which do not substantially affect the activity of the various embodiments of this invention are also included within the definition of the invention provided herein. Accordingly, the following examples are intended to illustrate but not limit the present invention.

EXAMPLE I

Construction of Modular Lentiviral Targeting Vectors

This example shows the generation of a lentiviral targeting vector that separates the attachment and fusion functions of the lentiviral envelope protein into different polypeptides.

Lentiviral vectors coexpressing an affinity ligand for cell specific targeting and attachment and a fusogenic polypeptide for vector transduction were produced using two different affinity ligands for targeting. Briefly, the targeting polypeptide was generated by fusing a transmembrane anchoring domain with either human transferrin (hTf) or apolipoprotein E4 (ApoE4) binding domains. The transmembrane domain and cytoplasmic tail of human CD40 polypeptide was used as the anchoring portion of the targeting polypeptide because it is efficiently incorporated into the HIV envelope upon maturation. Lentiviral vectors expressing either the hTf-CD40 or the ApoE4-CD40 chimeric targeting polypeptides were generated as described below.

To produce the chimeric hTf-CD40 targeting polypeptide nucleic acid vector, or plasmid, amino acids corresponding to the transmembrane domain of CD40 were fused in frame to amino acids corresponding to human transferrin. To produce the chimeric ApoE4-CD40 targeting polypeptide nucleic acid vector, or plasmid, amino acids corresponding to the transmembrane domain of CD40 were fused in frame to amino acids corresponding to apolipoprotein E4.

The packaging construct used was a split packaging genome system essentially as described by Dull et al., supra. Briefly, a tat-defective packaging construct pCMVR8.93 was first generated by swapping an EcoRI-SacI fragment from plasmid R7/pneo(−), Feinberg et al., *Proc. Natl. Acad. Sci. USA*, 88:4045–49 (1991), with the corresponding fragment of pCMVR8.91, a previously described plasmid expressing Gag, Pol, Tat, and Rev, Zufferey et al., *Nat. Biotechnol*., 15:871–75 (1997). This fragment has a deletion affecting the initiation codon of the tat gene and a frameshift created by the insertion of an MluI linker into the Bsu36I.

Next, pMDLg/p was generated, which is a CMV-driven packaging construct that contains only the gag and pol coding sequences from HIV-1. First, pkat2Lg/p was constructed by ligating a 4.2-kb ClaI-EcoRI fragment from pCMVR8.74 with a 3.3-kb EcoRI-HindIII fragment from pkat2, Finer et al., Blood 83:43–50 (1994), and a 0.9-kb HindIII-NcoI fragment from pkat2 along with an NcoI-ClaI linker consisting of synthetic oligonucleotides

```
5'-CATGGGTGCGAGAGCGTCAGTATTAAGCGGGGGAGAATTAG
AT-3'(SEQ ID NO: 1)
and

5'-CGATCTAATTCTCCCCCGCTTAATACTGACGCTCTCGCACC-3'.
(SEQ ID NO: 2)
``` pCMVR8.74 is a derivative of pCMVR8.91, described above, in which a 133-bp SacII fragment, containing a splice donor site, has been deleted from the CMV-derived region upstream of the HIV sequences to optimize expression. Second, pMDLg/p was constructed by inserting the 4.25-kb EcoRI fragment from pkat2Lg/p into the EcoRI site of pMD-2. pMD-2 is a derivative of pMD.G, Ory et al., *Proc. Natl. Acad. Sci. USA*, 93:11400–406 (1996), in which the pXF3 plasmid backbone of pMD.G has been replaced with a minimal pUC plasmid backbone and the 1.6-kb VSV G-encoding EcoRI fragment has been removed.

Finally, packaging construct pMDLg/pRRE was produced, which differs from pMDLg/p by the addition of a 374-bp RRE-containing sequence from HIV-1 (HXB2) immediately downstream of the pol coding sequences. To generate pMDLg/pRRE, the 374-bp NotI-HindIII RRE-containing fragment from pHR3 was ligated into the 9.3-kb NotI-BglII fragment of pVL1393 (Invitrogen, San Diego, Calif.) along with a HindIII-BglII oligonucleotide linker consisting of synthetic oligonucleotides 5'-AGCTTCCGCGGA-3' (SEQ ID NO: 3) and 5'-GATCTCCGCGGA-3' (SEQ ID NO: 4) to generate pVL1393RRE (pHR3 was derived from pHR2 by the removal of HIV env coding sequences upstream of the RRE sequences in pHR2, where pHR2 is a transducing vector described below in Example II). A NotI site remains at the junction between the gag and RRE sequences. pMDLg/pRRE was then constructed by ligating the 380-bp EcoRI-SstII fragment from pV1393RRE with the 3.15-kb SstII-NdeI fragment from pMD-2FIX (pMD-2FIX is a human factor IX-containing variant of pMD-2 which has an SstII site at the 3' end of the factor IX insert), the 2.25-kb NdeI-AvrII fragment from pMDLg/p, and the 3.09-kb AvrII-EcoRI fragment from pkatlLg/p, Finer et al., supra.

The second plasmid construct of the split packaging system consists of a nucleic acid vector expressing the rev gene product. pRSV-Rev and pTK-Rev are two such rev cDNA-expressing plasmids in which the joined second and third exons of HIV-1 rev are under the transcriptional control of the RSV U3 and herpes simplex virus type 1 thymidine kinase (TK) promoters, respectively. Both expression plasmids utilize polyadenylation signal sequences from the HIV LTR in a pUC 118 plasmid backbone. Dull et al., supra.

Lentiviral vectors incorporating the hTf-CD40 or ApoE4-CD40 chimeric targeting polypeptides into their envelopes were produced by co-transfection of the corresponding nucleic acid vectors together with a packaging construct. Transient transfection of the plasmid constructs into 293T cells was performed essentially as described by Naldini et al., Science 272:263–267 (1996). Briefly, a total of $5 \times 10^6$ 293T cells were seeded in 10-cm-diameter dishes 24 hours (h) prior to transfection in Iscove modified Dulbecco culture medium (JRH Biosciences) with 10% fetal bovine serum, penicillin (100 IU/ml), and streptomycin (100 µg/ml) in a 5% CO2 incubator, and the culture medium was changed 2 h prior to transfection. A total of 20 µg of plasmid DNA was used for the transfection of one dish: 3.5 µg of the targeting polypeptide plasmid hTf-CD40 or ApoE4-CD40 6.5 µg of packaging plasmid, and 10 µg of transducing vector plasmid. Where both targeting polypeptide and fusogenic polypeptide were expressed simultaneously to produce a lentiviral vector exhibiting separate attachment and fusion functions, as described below, about equal molar ratios of targeting polypeptide plasmid and fusogenic polypeptide plasmid were used, respectively.

The precipitate for transfection was formed by adding the plasmids to a final volume of 450 µl of 0.1×TE (1×TE is 10 mM Tris (pH 8.0) plus 1 mM EDTA) and 50 µl of 2.5 M CaCl2, mixing well, then adding dropwise 500 µl of 2×HEPES-buffered saline (281 mM NaCl, 100 mM HEPES, 1.5 mM Na2HPO4 (pH 7.12)) while vortexing and immediately adding the precipitate to the cultures. The medium (10 ml) was replaced after 14 to 16 h; the conditioned medium was collected after another 24 h, cleared by low-speed centrifugation, and filtered through 0.22-µm-pore-size cellulose acetate filters. For in vitro experiments, serial dilutions of freshly harvested conditioned medium were used to infect $10^5$ cells in a six-well plate in the presence of Polybrene (8 µg/ml). Viral p24 antigen concentration was determined by immunocapture using commercially available kits (Alliance; DuPont-NEN). Vector batches were tested for the absence of replication-competent virus by monitoring p24 antigen expression in the culture medium of transduced SupT1 lymphocytes for 3 weeks. In all cases tested, p24 was undetectable (detection limit, 3 pg/ml) once the input antigen had been eliminated from the culture. Transducing activity was expressed in transducing units (TU). Concentrated and purified lentiviral vector particles expressing the hTF-CD40 attachment polypeptide tested positive for the transferrin protein by protein blot.

Figure 2:
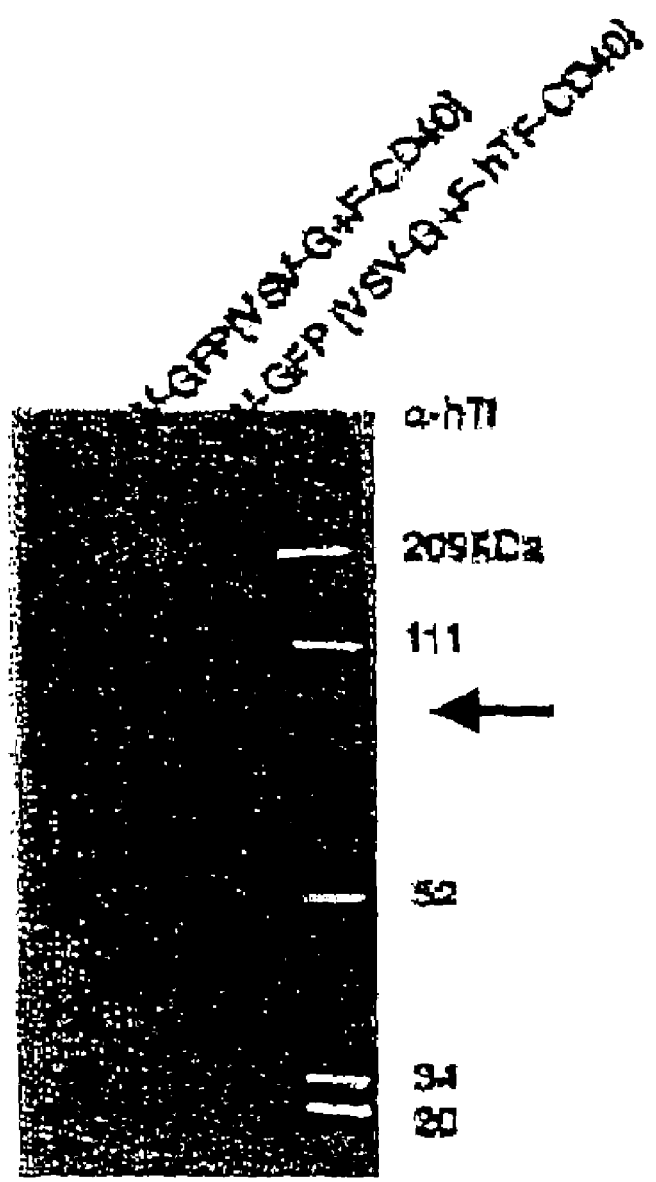
FIG. 2 shows a protein blot of a lentiviral vector constituents expressing a human transferrin targeting polypeptide.

Lentiviral vectors have been generated utilizing fusogenic polypeptides that are either attachment incompetent or that additionally contain attachment activity. The fusogenic polypeptides utilized include, VSV-G, Rabies-G, HIV gp160, HIV gp41 and a binding deficient influenza hemagluttinin. The VSV-G fusion protein still retains the ubiquitous binding activity, so this targeting polypeptide was used to verify incorporation of the heterologous or chimeric targeting polypeptides. The nucleic acid vector used for this transfection was pMD.G, Ory et al., supra. Incorporation was verified by harvesting lentiviral vector containing supernatant and concentrating by high speed centrifugation. The vector particles were further purified by centrifugation over a 20% sucrose cushion. The resulting lentiviral vector pellet was loaded onto a poly-acrylamide gel, electrophoresed and blotted to PVDF membrane. The protein blot was probed with an anti-human transferrin antibody. The results are shown in FIG. 2 where the arrow indicates the location of human transferring-CD40 targeting polypeptide.

The Rabies-G fusogenic polypeptide is similar to VSV-G in that it also retains its binding activity. However, differs in that it exhibits binding activity specifically to neurons. Therefore, the Rabies-G polypeptide confers both fusogenic and neuronal specific binding properties onto the resultant vector particle. Lentiviral vectors were generated as described above that co-express both the transferrin chimeric targeting polypeptide as an affinity ligand and the Rabies-G polypeptide.

To test the targeting efficiency of the hTf-CD40 targeting vectors containing the Rabies-G fusogenic polypeptide, the vector particles were injected intra-venously into mice and then three weeks later, the brains of the mice were analyzed for virus transduction. Mice infected with the lentiviral vector containing only the Rabies-G protein did not infect neurons in the brain due to the blood-brain barrier. However, vectors containing both the transferrin targeting polypeptide and the Rabies-G fusogenic polypeptide infect cells in the brain, albeit at a low efficiency. Because these vectors were able to cross the blood brain barrier while those expressing only the fusogenic polypeptide did not, the conclusion is that the hTf targeting polypeptide facilitated penetration of the blood-brain barrier via binding to the transferrin receptor expressed on the endothelial cells.

Lentiviral targeting vectors co-expressing a targeting polypeptide with either the HIV gp160 envelope polypeptide or the HIV gp41 fusogenic domain of gp160 were also produced. In this regard, the fully processed HIV gp160 envelope protein contains the attachment function in the gp120 protein and the fusion function in the membrane bound gp41 protein. During high speed centrifugation, used to concentrate the virus, the disulfide linked gp120 protein is sheared off the virus envelope, leaving only the gp41 fusion protein.

Lentiviral vectors were generated with the transferrin or ApoE4 affinity binding domain as the targeting polypeptide and the gp160 envelope protein. These vectors were further subjected to concentration by high speed centrifugation to ultimately generate vectors containing the transferrin or ApoE targeting polypeptides and the gp41 fusogenic polypeptide. The resultant lentiviral vectors were used to transduce HepG2 cells, an immortalized human hepatocyte cell line, as described previously to demonstrate targeting and transduction efficiency.

Figure 3:
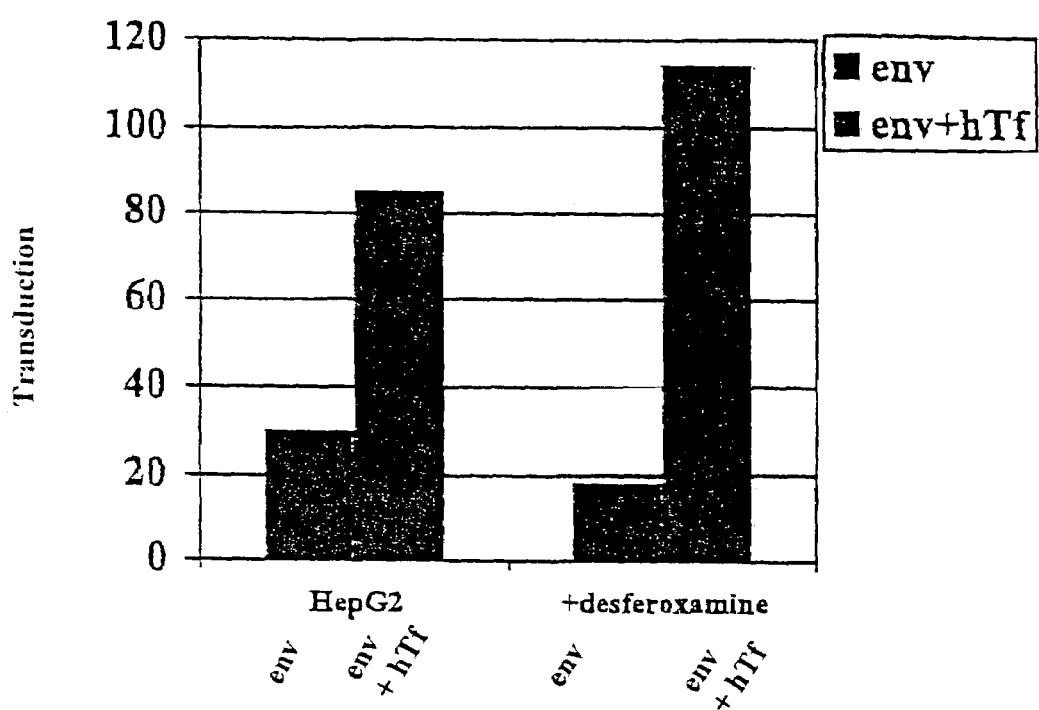
FIG. 3 shows the targeting of a lentiviral vector expressing a fusogenic polypeptide and a human transferrin targeting polypeptide and transduction of transferrin receptor expressing cells.

Briefly, HepG2 cells were transduced with vectors containing the gp41 fusion protein alone or with the transferrin attachment protein in the absence or presence of 5 M desforoxamine, which is an iron chelating agent known to upregulate the transferrin receptor. The results are shown in FIG. 3. Vectors containing the transferrin targeting polypeptide transduced approximately 3 times more HepG2 cells compared to vectors expressing the gp41 fusogenic polypeptide alone (FIG. 3, left histogram). Addition of desferoxamine to upregulate the transferrin receptor increased the transduction efficiency of the vector containing the transferrin targeting polypeptide a further 1.5 fold without affecting the efficiency of the vector expressing gp41 alone (FIG. 3, right histogram).

Figure 4:
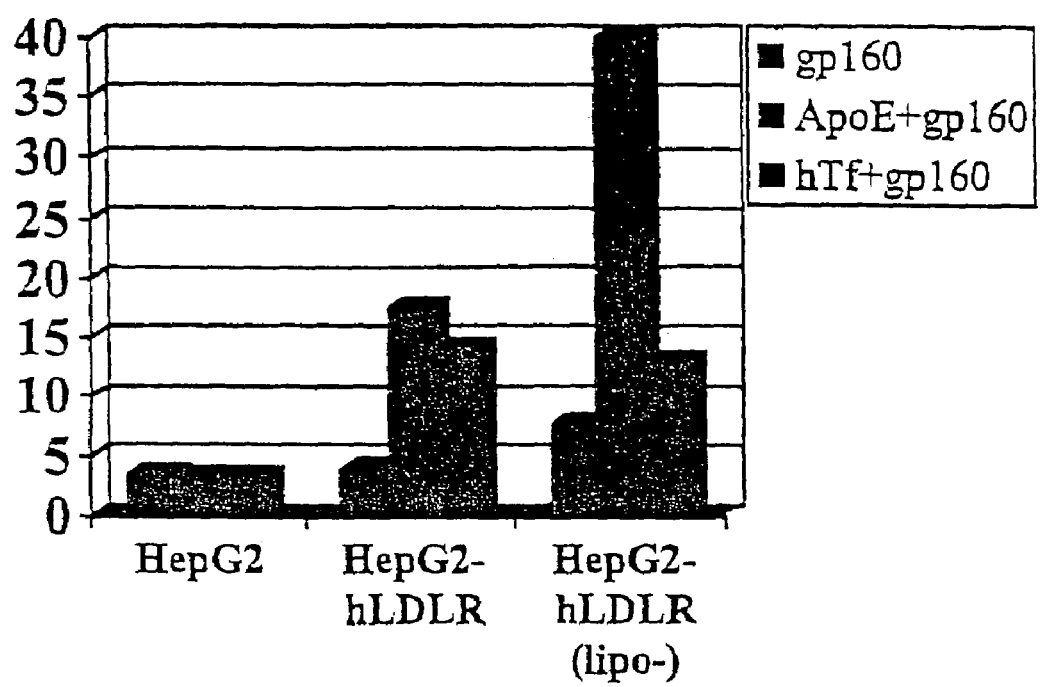
FIG. 4 shows the targeting of a lentiviral vector expressing a fusogenic polypeptide and an apolipoprotein E4 targeting polypeptide and transduction of LDL receptor expressing cells.

To test the transduction efficiency of the ApoE-CD40 lentiviral vector, a HepG2 cell line that constitutively expresses the LDL receptor (LDLR) was generated. To further upregulate the surface expression of the LDLR, cells were grown in lipoprotein deficient serum. The HepG2 cells constitutively expressing LDLR (HepG2-hLDLR) were transduced by the ApoE-CD40 vector as described previously. The results are shown in FIG. 4 and demonstrate an increased transduction by vectors that contained the hTf-CD40 or ApoE-CD40 and gp41 fusion protein compared to vector particles that contained the gp41 fusion protein alone (FIG. 4, middle histogram (HepG2-hLDLR)). HepG2 cells lacking the LDLR were used as a control and showed little preference between viral vectors lacking a specific targeting polypeptide (FIG. 4, left histogram (HepG2)). Further, upregulation of the endogenous LDLR receptor by culturing in lipoprotein deficient serum resulted in an additional two-fold increase in transduction efficiency by the vector containing the ApoE-CD40 attachment protein (FIG. 4, right histogram (HepG2-hLDLR(lipo-)). This increase in transduction efficiency was not observed for the lentiviral vector containing the hTf-CD40 attachment protein nor the vector containing the gp41 fusion protein alone.

The results above demonstrate the ability to target the lentiviral vectors containing the transferrin or LDLR ligand to cells expressing the respective receptor, the efficiency of transduction is lower than would be expected if most of the gp160 envelope protein were converted to the gp41 fusogenic polypeptide species. Analysis of the p24 antigen content within the vector pellets indicated that vector particles was produced at sufficient titers (e.g., $1 \times 10^9 – 2 \times 10^{10}$ tdu/ml). Therefore, the lower than expected transduction efficiency is likely due to insufficient fusogenic polypeptide present on the vector surface. For example, residual gp120 bound to gp41 could inhibit efficient fusion. However, there are no convenient methods for determining the efficiency of shearing off gp120 during the high speed centrifugation step.

Lentiviral vectors co-expressing the hTf-CD40 or the ApoE-CD40 targeting polypeptides and a binding deficient, fusion competent influenza hemagluttinin potein (HA) as the fusogenic polypeptide also have been construced. Briefly, a number of binding deficient, fusion competent influenza HA variant proteins have been described by Lin and Cannon (*Virus Res.*, 83:43–5 (2002); Lin et al., *Hum. Gene Therapy*, 12:323–32 (2001)). Such genetically modified forms of HA from the avian influenza virus A/FPV/Rostock/34 have been demonstrated to retain the fusion capacity of HA while abrogating the binding function. A triple mutant, designated HAtmt, was shown to incorporate into retroviral envelopes and functions as a fusion protein upon infection. Lentiviral vectors expressing the ApoE-CD40 or hTf-CD40 together with the HAtmt fusion protein can be tested on HepG2 cells in the presence or absence of desforoxamine (for the transferrin containing viruses) or lipoprotein deficient serum (for the ApoE containing viruses) as described above.

EXAMPLE II

Target Specific Transduction of Modular Lentiviral Targeting Vectors

This example describes the specific targeting and transduction of a cell with a vector genome harboring an expressible transgene.

The lentiviral targeting vectors described in Example I can be used for target specific transduction of a transgene of interest. The transgene can be contained in and expressed from the vector genome following packaging and delivery to target cells by the lentiviral vector.

A self-inactivating lentiviral transducing vector, or vector genome, can be used to deliver a desired gene to target cells. The self-inactivating vectors were generated from pHR'CMV-LacZ and pHR'CMV-Luciferase transfer vectors described by Naldini et al., supra, and Dull et al., *J. Virology*, 72:8463–71 (1998). pHR' is a letiviral transducing vector containing cis-acting sequences of HIV required for packaging, reverse transcription and integration. Briefly, this vector contains HIV 5' and 3' long terminal repeats (LTR), an HIV packaging signal, a Rev responsive element (RRE) and splice donor and acceptor sites. This transfer vector also contains a truncated and out of frame HIV gag gene and a CMV promoter that is used to drive expression of a transgene which can be cloned into a downstream unique restriction sites. Naldini et al., supra.

A derivative of pHR' is the pHR2 lentiviral transducing vector in which the polylinker and downstream nef sequences up to the KpnI site of pHR' have been replaced with a polylinker containing the restriction sites ClaI/SpeI/SnaBI/SmaI/BamHI/SacII/EcoRI as reported by Dull et al., supra. A transgene encoding a desired gene under the control of either murine PGK, human CMV or Moloney leukemia virus (MLV) promoters was inserted into the polylinker of pHR2 to yield the lentiviral transducing vectors pHR2PGK, pHR2CMV, and pHR2MFG, respectively.

pRRL, pRLL, pCCL, and pCLL are lentivirus transducing vectors containing chimeric Rous sarcoma virus (RSV)-HIV or CMV-HIV 5' LTRs and vector genome backbones in which an enhancerless simian virus 40 (SV40) polyadenylation and origin of replication sequences were included downstream of the HIV 3' LTR, replacing most of the human sequence remaining from the HIV integration site. In pRRL, the enhancer and promoter from the U3 region of RSV (nucleotides 233 to 1 relative to the transcriptional start site; GenBank accession no. J02342) are joined to the R region of the HIV-1 LTR. In pRLL, nucleotides 233 to 50 of the RSV enhancer sequences are joined to the promoter region at position 78 relative to the transcriptional start site of HIV-1. In pCCL, the enhancer and promoter of CMV (nucleotides 673 to 1 relative to the transcriptional start site; GenBank accession no. K03104) were joined to the R region of HIV-1. In pCLL, nucleotides 673 to 220 of the CMV enhancer was joined to the promoter region at position 78 of HIV-1.

Versions of the above lentiviral transducing vectors also were produced to express a transgene under the control of the human PGK promoter to produce pCCLhPGK, pCLLhPGK, pRRLhPGK, and pRLLhPGK. Briefly, a transgene was placed under the control of the human PGK promoter (nucleotides 5 to 516; GenBank accession no. M11958), and inserted into the polylinker region of each parental vector. pRRLGFP was obtained by deletion of the XhoI-BamHI fragment containing the PGK promoter from pRRLhPGK-GFP.

pRRLhPGK.SIN-18 is a vector in which 3' LTR sequences from 418 to 18 relative to the U3/R border have been deleted from pRLLhPGK.GFP, as described by Zufferey et al., *J. Virology*.

Lentiviral vectors containing a vector genome described above were packaged and isolated as described in Example I and used for transducing target cells with the transgene.

Throughout this application various publications have been referenced within parentheses. The disclosures of these publications in their entireties are hereby incorporated by reference in this application in order to more fully describe the state of the art to which this invention pertains.

Although the invention has been described with reference to the disclosed embodiments, those skilled in the art will readily appreciate that the specific experiments detailed are only illustrative of the invention. It should be understood that various modifications can be made without departing from the spirit of the invention. Accordingly, the invention is limited only by the following claims.

What is claimed is:

1. A lentiviral vector, comprising an attachment incompetent fusogenic polypeptide and a heterologous targeting polypeptide, wherein said attachment incompetent fusogenic polypeptide comprises lentivirus gp4 1 or a binding defective influenza hemagglutinin polypeptide, wherein said heterologous targeting polypeptide comprises a chimeric polypeptide that comprises a membrane attachment domain and a targeting domain, and wherein said membrane attachment domain comprises a transmembrane domain of CD40.

2. A lentiviral packaging construct comprising:

(a) a nucleic acid sequence encoding trans-acting factors sufficient for lentiviral vector generation and an attachment incompetent fusogenic polypeptide, wherein the encoded attachment incompetent fusogenic polypeptide comprises lentivirus gp41 or a binding defective influenza hemagglutinin polypeptide; and (b) a nucleic acid sequence encoding a heterologous targeting polypeptide comprising a chimeric polypeptide that comprises a membrane attachment domain and a targeting domain, wherein said membrane attachment domain comprises a transmembrane domain of CD40.

3. The lentiviral packaging construct of claim 2, wherein said trans-acting factors sufficient for lentiviral vector generation comprise lentiviral gag, pol and rev.

4. The lentiviral packaging construct of claim 3, wherein at least one trans-acting factor sufficient for lentiviral vector generation is encoded on a separate nucleic acid vector.

5. A lentiviral packaging system having at least three nucleic acid vectors, comprising:

(a) a first nucleic acid vector comprising a packaging construct encoding a trans-acting factor for lentiviral vector generation, (b) a second nucleic acid vector encoding an attachment incompetent fusogenic polypeptide comprising lentivirus gp41 or a binding defective influenza hemagglutinin polypeptide, said first and second nucleic acid vectors together encoding trans-acting factors sufficient for lentiviral vector generation, and, (c) a third nucleic acid vector comprising a nucleic acid sequence encoding a heterologous targeting polypeptide, wherein said heterologous targeting polypeptide comprises a chimeric polypeptide comprising a membrane attachment domain and a targeting domain, and wherein said membrane attachment domain comprises a transmembrane domain of CD40.

6. The lentiviral packaging system of claim 5, wherein said trans-acting factor sufficient for lentiviral vector generation comprise lentiviral gag, pol and rev.

7. The lentiviral packaging construct of claim 6, wherein at least one trans-acting factor sufficient for lentiviral vector generation is encoded on a separate nucleic acid vector.

8. A lentiviral gene delivery system having at least four nucleic acid vectors, comprising:

(a) a first nucleic acid vector comprising a packaging construct encoding a trans-acting factor for lentiviral vector generation:

(b) a second nucleic acid vector comprising a fusogenic construct encoding an attachment incompetent fusogenic polypeptide comprising lentivirus gp41 or a binding defective influenza hemagglutinin polypeptide:

(c) a third nucleic acid vector comprising a lentiviral vector genome encoding lentiviral cis sequences sufficient for vector genome transduction, said first, second and third nucleic acid vectors together encoding trans-acting factors sufficient for lentiviral vector generation; and, (d) a fourth nucleic acid vector comprising a nucleic acid sequence encoding a heterologous targeting polypeptide comprising a chimeric polypeptide comprising a membrane attachment domain and a targeting domain, wherein said membrane attachment domain comprises a transmembrane domain of CD40.

9. The lentiviral gene delivery system of claim 8, wherein said trans-acting factor of (a) sufficient for lentiviral vector generation comprises lentiviral gag, pol and rev.

10. The lentiviral gene delivery system of claim 9, wherein at least one trans-acting factor sufficient for lentiviral vector generation is encoded on a separate nucleic acid vector.

11. The lentiviral gene delivery system of claim 8, wherein said cis sequences sufficient for vector genome transduction are selected from the group consisting of a packaging signal, a genome integration sequence, a replication promoter, post-transcriptional cis sequences, post-translational cis sequences, and an expression cassette.

* * * * *

SEQUENCE LISTING

<160> NUMBER OF SEQ ID NOS: 4

<210> SEQ ID NO 1
<211> LENGTH: 43
<212> TYPE: DNA
<213> ORGANISM: Artificial Sequence
<220> FEATURE:
<223> OTHER INFORMATION: synthetic oligonucleotide

<400> SEQUENCE: 1
catgggtgcg agagcgtcag tattaagcgg gggagaatta gat          43

<210> SEQ ID NO 2
<211> LENGTH: 41
<212> TYPE: DNA
<213> ORGANISM: Artificial Sequence
<220> FEATURE:
<223> OTHER INFORMATION: synthetic oligonucleotide

<400> SEQUENCE: 2
cgatctaatt ctcccccgct taatactgac gctctcgcac c            41

<210> SEQ ID NO 3
<211> LENGTH: 12
<212> TYPE: DNA
<213> ORGANISM: Artificial Sequence
<220> FEATURE:
<223> OTHER INFORMATION: synthetic oligonucleotide

<400> SEQUENCE: 3
agcttccgcg ga                                             12

<210> SEQ ID NO 4
<211> LENGTH: 12
<212> TYPE: DNA
<213> ORGANISM: Artificial Sequence
<220> FEATURE:
<223> OTHER INFORMATION: synthetic oligonucleotide

<400> SEQUENCE: 4
gatctccgcg ga                                             12